United States Patent
Merz, Jr. et al.

(10) Patent No.: US 9,483,609 B2
(45) Date of Patent: Nov. 1, 2016

(54) PHARMACOGENIC THERAPIES TARGETING THE METAL-ION TRANSCRIPTIONAL REGULATION MACHINERY IN BACTERIA

(71) Applicant: UNIVERSITY OF FLORIDA RESEARCH FOUNDATION, INCORPORATED, Gainesville, FL (US)

(72) Inventors: Kenneth Malcolm Merz, Jr., Gainesville, FL (US); Dhruva Chakravorty, Holt, MI (US)

(73) Assignee: UNIVERSITY OF FLORIDA RESEARCH FOUNDATION, INCORPORATED, Gainesville, FL (US)

(*) Notice: Subject to any disclaimer, the term of this patent is extended or adjusted under 35 U.S.C. 154(b) by 0 days.

(21) Appl. No.: 14/769,587

(22) PCT Filed: Mar. 11, 2014

(86) PCT No.: PCT/US2014/022921
§ 371 (c)(1),
(2) Date: Aug. 21, 2015

(87) PCT Pub. No.: WO2014/159308
PCT Pub. Date: Oct. 2, 2014

(65) Prior Publication Data
US 2016/0004812 A1    Jan. 7, 2016

Related U.S. Application Data

(60) Provisional application No. 61/784,409, filed on Mar. 14, 2013.

(51) Int. Cl.
*G06F 19/12* (2011.01)
*G01N 33/68* (2006.01)
*G06F 19/00* (2011.01)
*A61K 31/519* (2006.01)

(52) U.S. Cl.
CPC ............. *G06F 19/12* (2013.01); *A61K 31/519* (2013.01); *G01N 33/6875* (2013.01); *G06F 19/706* (2013.01)

(58) Field of Classification Search
CPC ...................................................... G06F 19/12
USPC .................................................... 514/252.16
See application file for complete search history.

(56) References Cited

FOREIGN PATENT DOCUMENTS

WO    WO 2004/102159    11/2004

OTHER PUBLICATIONS

Arunkumar, A.I., et al., "Solution structure of a paradigm ArsR family zinc sensor in the DNA-bound state," *Proceedings of the National Academy of Sciences USA*, Oct. 27, 2009, vol. 106, No. 43, pp. 18177-18182.

Chakravorty, D.K., et al., "Energetics of Zinc-Mediated Interactions in the Allosteric Pathways of Metal Sensor Proteins," *Journal of the American Chemical Society*, 2013, vol. 135, pp. 30-33.

Chakravorty, D.K., et al., "Simulations of Allosteric Motions in the Zinc Sensor CzrA," *Journal of the American Chemical Society*, 2012, vol. 134, pp. 3367-3376.

Eicken, C., et al., "A Metal-Ligand-mediated Intersubunit Allosteric Switch in Related SmtB/ArsR Zinc Sensor Proteins," *Journal of Molecular Biology*, 2003, vol. 333, pp. 683-695.

Giedroc, D.P., et al., "Metal sensor proteins: nature's metal-loregulated allosteric switches," *Dalton Transactions*, 2007, pp. 3107-3120.

Grossoehme, N.E., et al., "Energetics of Allosteric Negative Coupling in the Zinc Sensor *S. aureus* CzrA," *Journal of the American Chemical Society*, 2009, vol. 131, pp. 17860-17870.

Guerra, A.J., et al., "Crystal Structure of the Zinc-Dependent MarR Family Transcriptional Regulator AdcR in the Zn(II)-Bound State," *Journal of the American Chemical Society*, 2011, vol. 133, pp. 19614-19617.

Guerra, A.J., et al., "Metal site occupancy and allosteric switching in bacterial metal sensor proteins," *Archives of Biochemistry and Biophysics*, 2012, vol. 519, pp. 210-222.

Harvie, D.R., et al., "Predicting metals sensed by ArsR-SmtB repressors: allosteric interference by a non-effector metal," *Molecular Microbiology*, 2006, vol. 59, No. 4, pp. 1341-1356.

Hood, M.I., et al., "Identification of an *Acinetobacter baumannii* Zinc Acquisition System that Facilitates Resistance to Calprotectin-mediated Zinc Sequestration," *PLOS Pathogens*, Dec. 2012, vol. 8, No. 12, Article No. e1003068, pp. 1-17.

Hood, M.I., et al., "Nutritional immunity: transition metals at the pathogen-host interface," *Nature Reviews Microbiology*, Aug. 2012, vol. 10, pp. 525-537.

(Continued)

*Primary Examiner* — Taofiq A Solola
(74) *Attorney, Agent, or Firm* — Saliwanchik, Lloyd & Eisenschenk (57) ABSTRACT

The subject invention pertains to methods of identifying compounds that bind to a binding pocket on metal ion binding proteins of the ArsR/SmtB family and modulate their regulatory activity by increasing the propensity of the proteins to remain in a conformationally trapped form such as the metal ion bound conformation or disulfide-linked conformation, the DNA bound conformation, or the apo-conformation. The invention provides methods of identifying such compounds using computer software programs. The invention also provides bioassays for identifying such compounds. The invention also provides pharmaceutical compositions containing compounds that modulate metal-loregulatory activities of the metal ion binding proteins of the ArsR/SmtB family.

14 Claims, 10 Drawing Sheets
(5 of 10 Drawing Sheet(s) Filed in Color)

(56) References Cited

OTHER PUBLICATIONS

Lee, C.W., et al., "Solution Structure of *Mycobacterium tuberculosis* NmtR in the Apo State: Insights into Ni(II)-Mediated Allostery," *Biochemistry*, 2012, vol. 51, pp. 2619-2629.

Ma, Z., et al., "Coordination Chemistry of Bacterial Metal Transport and Sensing," *Chemical Reviews*, 2009, vol. 109, pp. 4644-4681.

Ma, Z., et al., "Unnatural Amino Acid Substitution as a Probe of the Allosteric Coupling Pathway in a Mycobacterial Cu(I) Sensor," *Journal of the American Chemical Society*, 2009, vol. 131, pp. 18044-18045.

Osman, D., et al., "Bacterial metal-sensing proteins exemplified by ArsR-SmtB family repressors," *Natural Product Reports*, 2010, vol. 27, pp. 668-680.

Pennella, M.A., et al., "Structural elements of metal selectivity in metal sensor proteins," *Proceedings of the National Academy of Sciences USA*, Apr. 1, 2003, vol. 100, No. 7, pp. 3713-3718.

Reyes-Caballero, H., et al., "Metalloregulatory proteins: Metal selectivity and allosteric switching," *Biophysical Chemistry*, 2011, vol. 156, pp. 103-114.

Rogers, J.L., et al., "Development of Inhibitors of the PAS-B Domain of the HIF-2α Transcription Factor," *Journal of Medicinal Chemistry*, 2013, vol. 56, pp. 1739-1747.

Scheuermann, T.H., et al., "Allosteric inhibition of hypoxia inducible factor-2 with small molecules," *Nature Chemical Biology*, Apr. 2013, vol. 9, pp. 271-278.

Written Opinion in International Application No. PCT/US2014/022921, Jul. 3, 2014, pp. 1-6.

PHARMACOGENIC THERAPIES TARGETING THE METAL-ION TRANSCRIPTIONAL REGULATION MACHINERY IN BACTERIA

CROSS-REFERENCE TO RELATED APPLICATIONS

This application is the U.S. national stage application of International Patent Application No. PCT/US2014/022921, filed Mar. 11, 2014, which claims the benefit of U.S. Provisional Application Ser. No. 61/784,409, filed Mar. 14, 2013, the disclosures of which are hereby incorporated by reference in their entirety, including all figures, tables and amino acid or nucleic acid sequences.

This invention was made with government support under GM044974 and GM066859 awarded by National Institutes of Health. The government has certain rights in the invention.

BACKGROUND OF THE INVENTION

Metal ions are essential for their diverse roles in biological processes but are lethal at high concentrations.[1,2] The complex machinery of metal ion homeostasis (MH) maintains optimal cellular concentrations of metal ions and is critical for the survival of living organisms.[2] In some pathogenic bacteria, the MH machinery confers antibiotic resistance, making it imperative to understand its mode of action. Metal ion sensing transcriptional regulators play the crucial role of controlling the expression of proteins that are involved in the uptake, transfer and efflux of metal ions in MH.[2] The ArsR/SmtB family of metal ion sensing transcriptional repressor proteins provides heavy metal resistance in pathogenic prokaryotic organisms like *Staphylococcus aureus, Mycobacterium tuberculosis, Listeria monocytogenes* and *Escherichia coli*.[2-4] These proteins have evolved from a common ancestry and are characterized by a helix-turn-helix fold. They function as transcriptional regulators by a mechanism of allosteric inhibition in which metal-ion binding or, alternatively, the formation of Cys-Cys disulfinde linkages triggers a conformational change that modulates their DNA-binding affinity. Understanding the mechanism of allosteric regulations and underlying changes in the structure and conformational dynamics of these proteins remains of fundamental interest. Effectively targeting this family of regulatory proteins would provide means to impair their heavy metal resistance and associated antibiotic resistance, potentially leading to novel therapeutic agents[1,5] and can be extended to target similar metal sensor proteins such as CsoR, NikR and AdcR.

BRIEF SUMMARY OF THE INVENTION

The invention concerns the energetics underlying the mechanism of allosteric regulation in the metal ion sensing and redox sensing proteins belonging to the ArsR/SmtB regulatory protein family.[4,6,7] The invention also concerns exploiting the allosteric mechanism to impair the allosteric mechanism of regulation operating in proteins belonging to the ArsR/SmtB family of transcription factors. The invention further provides novel compounds that bind to the proteins of the ArsR/SmtB family and impair their allosteric mechanism where the binding of the compound to a protein of the ArsR/SmtB family increases the propensity of the protein to remain in a conformationally locked form such as the metal ion bound form or di-sulfide linkage form, the DNA bound form, or the apo-form. Even further, the invention provides in silico methods for identifying compounds that will bind to the proteins of the ArsR/SmtB family and impair their regulatory mechanism by increasing the propensity of the protein to remain in the conformationally locked form such as the metal ion bound form or di-sulfide linkage form, the DNA bound form, or the apo-form. Furthermore, the invention provides bioassays for identifying compounds that will bind to the proteins of the ArsR/SmtB family and impair their metalloregulatory properties by increasing the propensity of the protein to remain in the metal ion bound form, the DNA bound form, or the apo-form.

BRIEF DESCRIPTION OF THE FIGURES

The patent or application file contains at least one drawing executed in color. Copies of this patent or patent application publication, with color drawing(s), will be provided by the Office upon request and payment of the necessary fee.

FIG. 6. Bioinformatics analysis of 3000 ArsR/SmtB family repressors. Residue-specific conservation plotted as relative entropy of residue positions 15-35, 41-87, 89-90 and 92-98 which correspond to CzrA residue positions. Gaps correspond to gaps in the multiple sequence alignment. Residues in the binding pockets shown in FIGS. 4 and 5 remain largely conserved across the family.

Normalized population distribution from 100 ns of MD of Ser54-Ser54' distances for apo-CzrA and KM-bound CzrA starting from the closed conformation. While apo-CzrA transitions to the open conformation, the KMC drug-like molecule forces CzrA to sample the closed conformation.

DETAILED DISCLOSURE OF THE INVENTION

Figure 1:
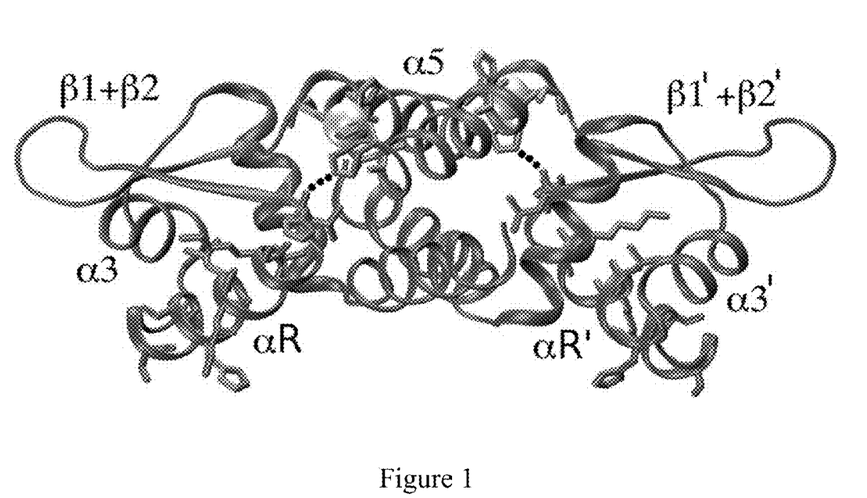
FIG. 1. Cartoon representation of Zn(II)-bound CzrA showing major secondary structural features (PDB code: 1R1V). Zinc ions are represented as silver spheres, and its ligating residues are shown in green. The H97-H67 hydrogen bonds are shown with dotted black lines. The residues involved in the hydrogen-bonding pathway are shown in blue licorice depiction.
Figure 2:
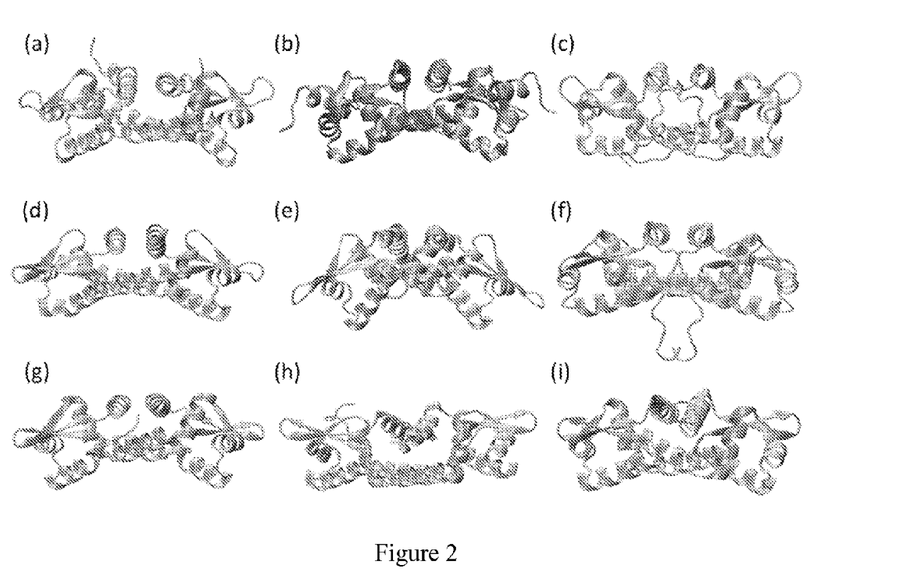
FIGS. 2a-2i. Cartoon representation of nine structurally characterized ArsR/SmtB family proteins. These proteins include (a) BigR, (b) CadC, (c) CmtR, (d) HlyU, (e) HypR, (f) NmtR, (g) PagR, (h) SmtB and (i) CzrA.

The metal-ion sensing members of the ArsR/SmtB family of transcriptional repressor proteins provide heavy metal resistance in pathogenic prokaryotic organisms.[8] Members of the ArsR/SmtB proteins bind metals at positions including the α5 and α3 binding sites that trigger an allosteric response in these proteins. An allosteric response would include a change in the structure or conformational dynamics of the protein, or both. CzrA (FIG. 1) is a well-characterized protein of the ArsR/SmtB family of transcriptional repressors, and is used as an example to explain the invention. CzrA exists in an "open" conformation in the apo-form and metal ion bound form, while adopting a "closed" conformation that increases its DNA binding affinity.[7,9,10] Other ArsR/SmtB proteins behave similarly to CzrA and are able to sample multiple conformational ensembles in the apo-allosteric form but prefer the open conformation.[7] Binding to a metal ion or forming a di-sulfide linkage quenches the conformational dynamics of these proteins, forcing them to remain in a conformationally and energetically locked open conformation.[7,9,10] In the metal ion bound form and di-sulfide linkaged forms, the proteins of the ArsR/SmtB family sample form limited conformational ensembles and are electrostatically less favorable for DNA binding.[7] Examples of metal ion sensing transcriptional repressor proteins in the ArsR/SmtB family include *Staphylococcus aureus* CzrA, *Staphylococcus aureus* pI258 CadC, *Mycobacterium tuberculosis* NmtR and *Synechococcus* spp. SmtB (FIG. 2). *Xylella fastidiosa* BigR is an example of a non-metal binding ArsR/SmtB protein that forms a conformationally trapped di-sulfide linkage form. The proteins share a helix-turn-helix fold that is common to the family. *Steptococcus pneumonia* AdcR of the MarR family of transcriptional regulators and *Mycobacterium tuberculosis* CsoR are other transcriptional factors involve a similar mechanism of action.

Correlation analysis of protein residue motions indicate that both metal binding sites and disulfide linkage sites in the proteins of the ArsR/SmtB family communicate with each other and metal binding and disulfide bond formation is also communicated to the DNA binding interface via a network of amino acid residues. A hydrogen bonding pathway (HBP), extending from the metal-ion binding regions to the DNA binding region (FIG. 1), has been implicated to play a major role in the mechanism of allosteric regulation in CzrA. A critical hydrogen bond that extends from the metal binding residue of the protein to the backbone carbonyl group of a histidine residue in the αR helix of the protein starts this pathway, and may only exist in metal bound forms or conformationally trapped disulfide linked allosteric forms of these proteins. Similar pathways have been found to be important in other metal ion sensing transcriptional repressors. For example, an HBP connecting the metal ion binding site to the DNA binding interface in the Cu(I) binding protein *M. tuberculosis* CsoR has been shown to be crucial for its allosteric function.[11] Similar hydrogen-binding pathways have been identified in the crystal structures of other Zn(II) bound forms *S. aureus* pI258 CadC and *Synechococcus* SmtB.[6,12,13] Such HBP may exist in Zn(II) *M. tuberculosis* NmtR as well.[4,6] A putative HBP linking the residue E24 of the major metal binding site to the residue Q40 was identified in the recently solved structures of Zn(II) transcriptional regulator *Streptococcus pneumonia* AdcR belonging to the multiple antibiotic resistance regulator (MarR) family of transcriptional regulators.[6,14]

Changes in the structure and conformational dynamics of the ArsR/SmtB family of proteins play an essential role in their mechanism of allosteric regulation.[9] An analysis of molecular dynamics (MD) trajectories of the apo-forms of CzrA, SmtB and NmtR indicates that the apo-form of these proteins samples the conformational phase-space of the zinc bound form and the DNA operator probably binds to the protein via an induced fit mechanism.[6] The allosterically silent α5 metal binding site-bearing CadC, however, functions differently.[15] Our MD simulations and NMR experiments suggest that the protein samples the closed DNA binding conformation in its apo-form.[6,8] These simulations show that the evolutionarily divergent CadC protein naturally has a higher DNA binding affinity in its apo-form, and remains closed in its metal bound form.[6] The similar conformational dynamics of the family of proteins are observed in the conserved patterns in the cross-correlation plots for these proteins, indicating that protein residues are involved in hierarchical networks of correlated and anti-correlated motions across the family of proteins.[7] These networks show that these proteins have channels of communication that allow the metal binding regions of the proteins to communicate to the DNA binding interfaces.

Drug molecules that disrupt the conformational dynamics of these proteins of the ArsR/SmtB family can be used to disrupt the allosteric mechanism of regulation operating within these proteins. Drug molecules have recently been shown to have similar effects on the HIF-2a transcription factor.[16,17] These drugs can stabilize or de-stabilize an allosteric form of these proteins, throwing the transcriptional machinery off-balance and creating a surplus or paucity of metal ions in the organism. The metalloregulatory proteins of the ArsR/SmtB family may be locked into a closed conformation in their metal-bound and apo-state on the introduction of these drugs, thus inhibiting the allosteric mechanism. Such drugs would provide a new class of antibiotics that could specifically target the transcriptional machinery in these organisms. These drugs can furthermore be designed to exploit the specific interactions that take place at the dimeric interface in these proteins of the ArsR/SmtB family.

Figure 3:
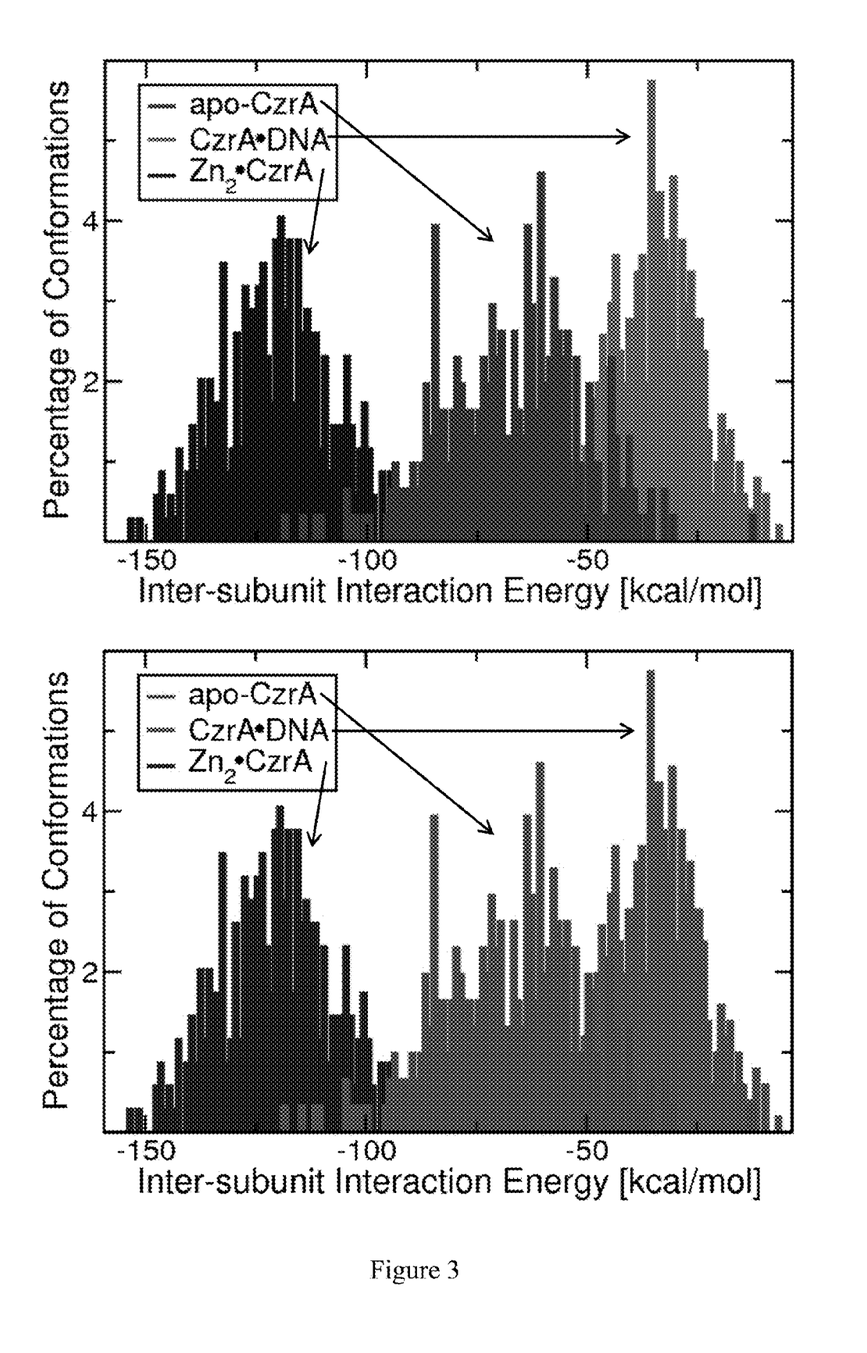
FIG. 3. Inter-subunit interaction energies for apo-, DNA bound, and zinc bound allosteric forms of CzrA. DNA binding weakens the inter-subunit interaction energies, while zinc binding strengthens them. Top panel is a greyscale version of the bottom panel provided in color.

Differences in the quaternary structures and conformational dynamics of the various allosteric forms of the proteins of the ArsR/SmtB family provide multiple and unique targets for drug molecules. The large amount of de-stabilization and flexibility in the protein's structure when bound to DNA may be exploited to bind drug molecules in the metal binding region of the protein, preventing the protein from achieving the low-DNA binding affinity conformational form (FIG. 1).[3,7,9] Conversely, the DNA binding interface of the protein may be affected to prevent DNA binding, thus preventing the protein from repressing the expression of the CzrB cation diffusion pump. Semi-empirical calculations suggest that the interactions at the dimer interface change in response to DNA binding or metal ion binding. (FIG. 3) Experimentally derived structures and trajectories from our MD and quantum mechanics/molecular mechanics (QM/MM) simulations provide a plethora of information on the structural dynamics of the proteins of the ArsR/SmtB family in their various allosteric forms.[4,6,7] These structural dynamics can be used to identify compounds which may bind to a protein of the ArsR/SmtB family and increase the propensity of the protein to remain in the metal ion bound form, the DNA bound form, or the apo-form. These compounds can be used as pharmaceutical agents to impair MH in pathogenic bacteria that use the proteins of the ArsR/SmtB family to maintain MH.

Figure 4:
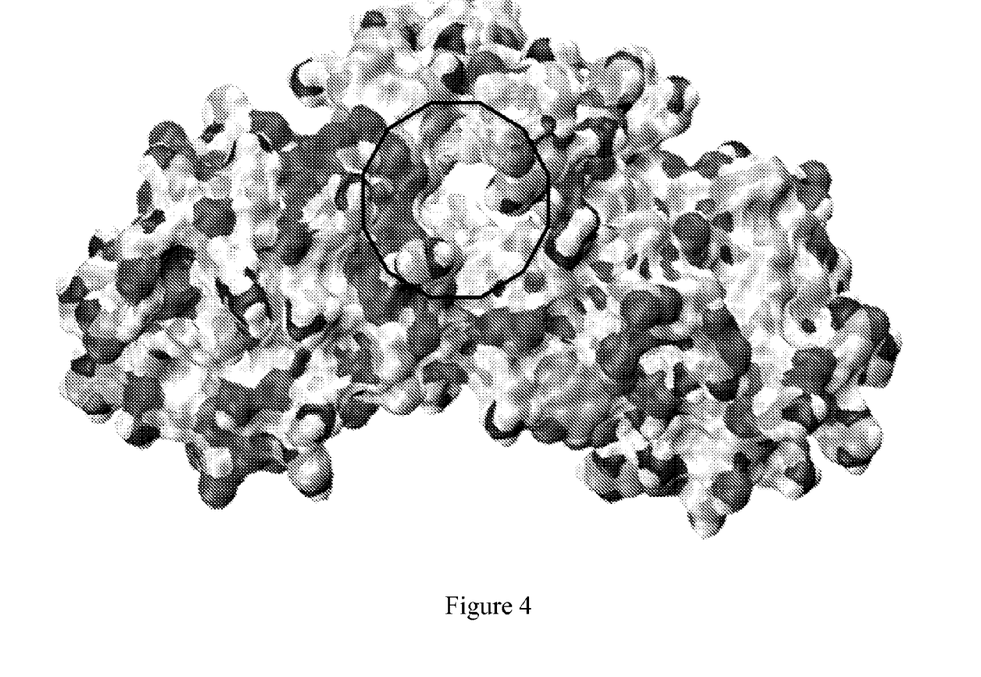
FIG. 4. Solvent accessible surface of CzrA in the DNA-bound allosteric form (pdb code: 2KJB). The drug docking pocket is shown using a black circle.
Figure 5A:
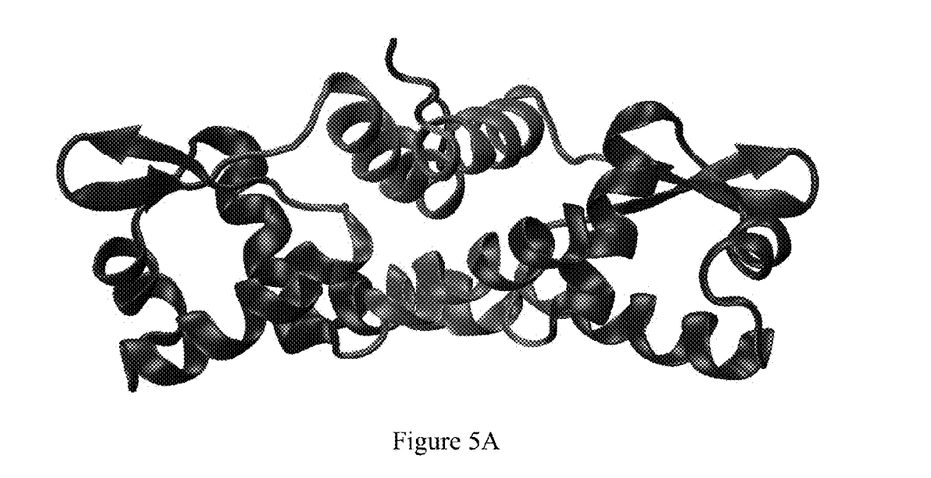
FIGS. 5A-5B. A cartoon representation of CzrA showing two drug binding sites. The volume elements described by the residues in red form the drug binding site. In figure (a) the pocket is described by residues 16 to 25, 66 to 70 and 82 to 100 of both protomers. In figure (b) the drug binding pocket is described by residues 42 to 79 of each protomer.
Figure 5B:
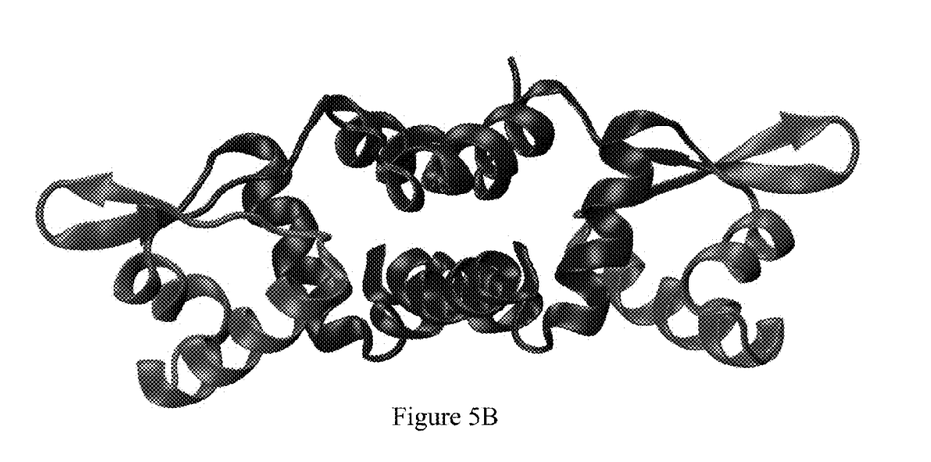
Figure 6:
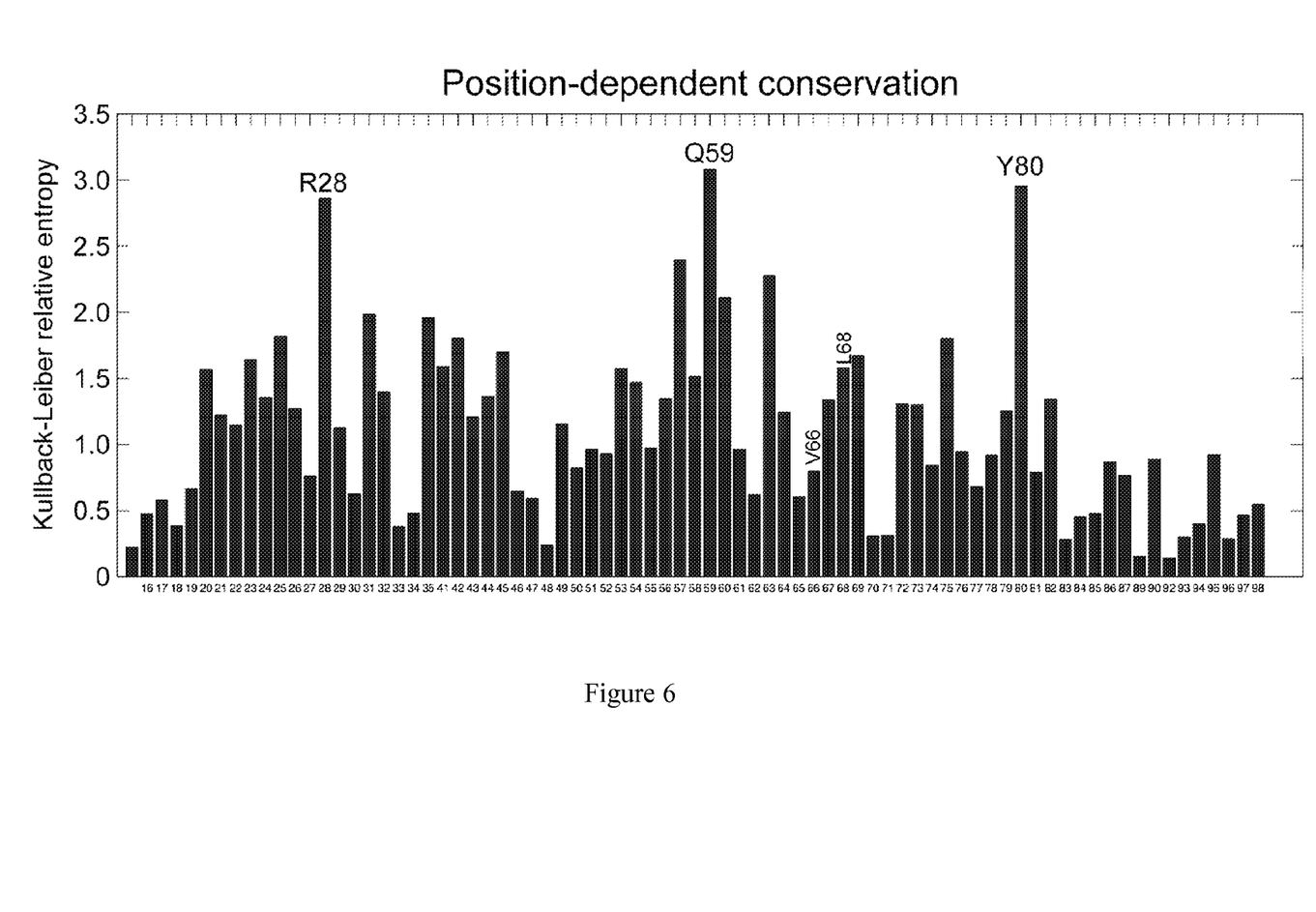

Drug efforts have been hampered by the lack of a traditional drug binding active site in these proteins. The similar energetics, structures and conformational dynamics of these critical metalloregulatory proteins provide us with an alternate route to impair the MH machinery in multiple pathogenic organisms. Impairment of the MH machinery by impairing the function of the metalloregulatory proteins may involve decreasing or increasing the binding affinity of these proteins to metal ions. In an aspect of the invention, computer modeling is used to identify compounds that bind to a novel pocket in proteins of the ArsR/SmtB family and increase the propensity of the proteins to remain in the conformationally locked metal ion bound form or di-sulfide linkaged form, the DNA bound form, or the apo-form. The pocket lies in the region between the metal-binding region and the operator-binding region of proteins of the ArsR/SmtB family (FIG. 4). This pocket may be described as a channel lying at the inter-sub-unit interface. This channel will be wider and more open in an allosteric form of the protein, but smaller and narrower in other allosteric forms. Drug molecules bound to this channel will disrupt interactions at these interfaces, finally effecting the allosteric mechanism. In the case of the ArsR/SmtB proteins, this pocket may be described as the channel between the α5 metal binding sites and the tips of the αR helices as shown in FIG. 4. This channel runs across the distance between the two metal binding sites and includes peripheral residues. In CzrA, this pocket is described as the channel whose boundaries are described by residues 16 to 25, 66 to 70 and 82 to 100 of both protomers (FIG. 5 ($a$)). Conservation of such pockets based on sequence similarity across the 3000 ArsR/SmtB family of proteins is depicted in FIG. 6. A second pocket may be described between residues 42 to 79 as shown in FIG. 5($b$). Computer modeling typically uses a docking program. A docking program is computer software which positions a small molecule ligand into a binding site on a protein molecule. Based on the positioning of the small molecule ligand into a binding site of the protein, the docking program can predict whether the small molecule ligand would bind to the binding site on the target protein according to the conventional binding characteristics of protein-ligand interactions.

Figure 7A:
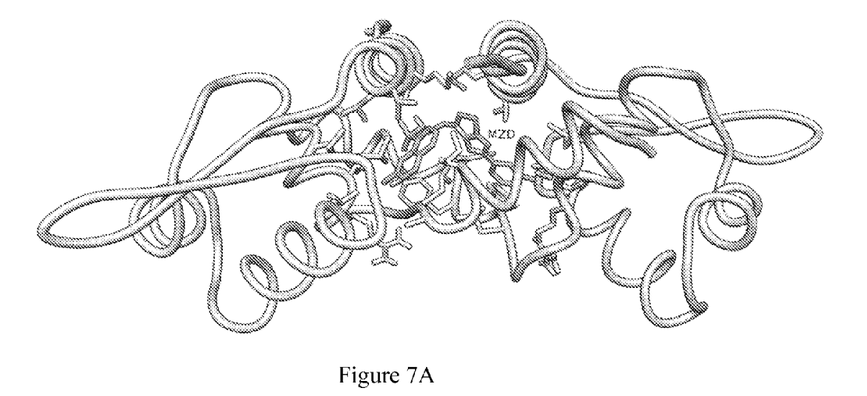
FIGS. 7A-7B. Images from 10 ns MD simulations of MZD in CzrA. The residues neighboring MZD are indicated in image (a). The molecule causes CzrA to remain in its closed conformation in our simulations.
Figure 7B:
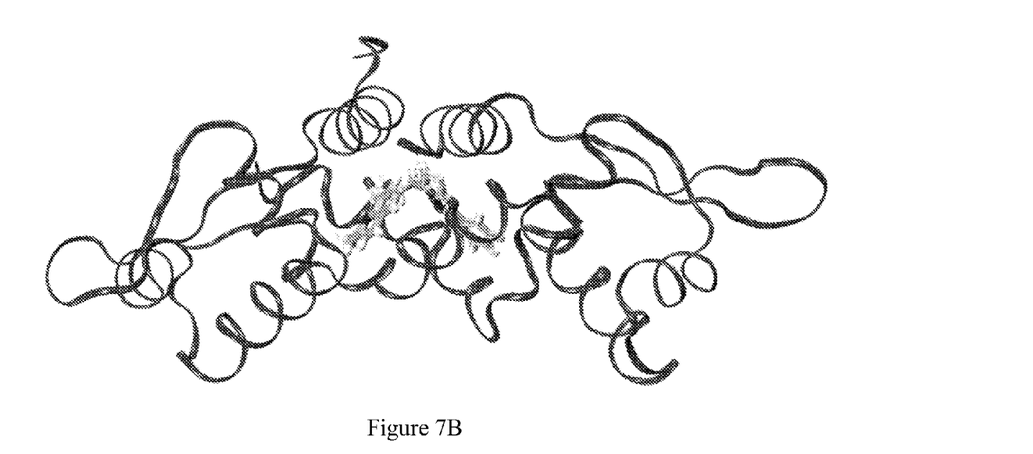
Figure 8:
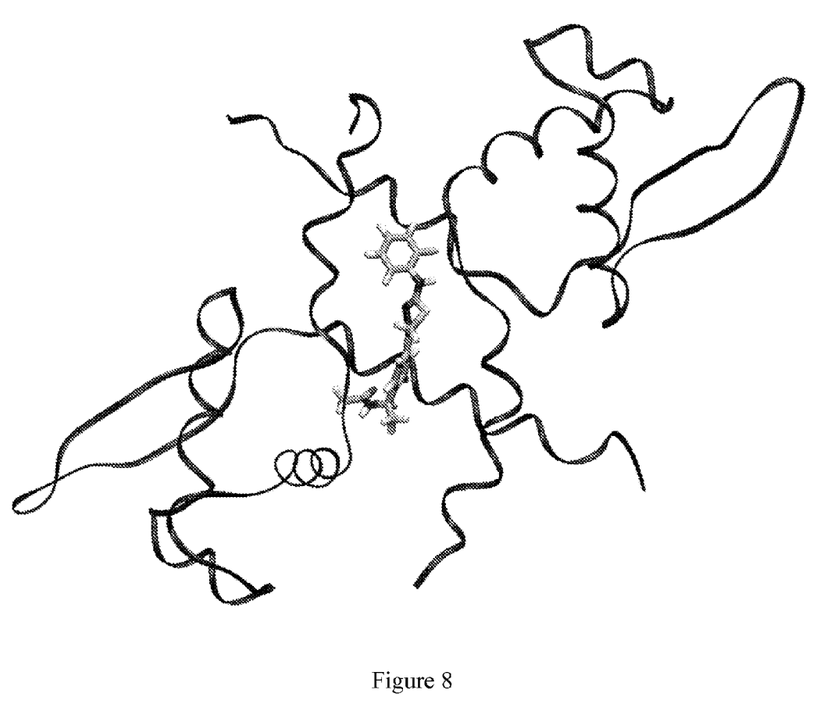
FIG. 8. Snapshot from MD trajectory of ZDI bound to the DNA binding interface of CzrA.
Figure 9:
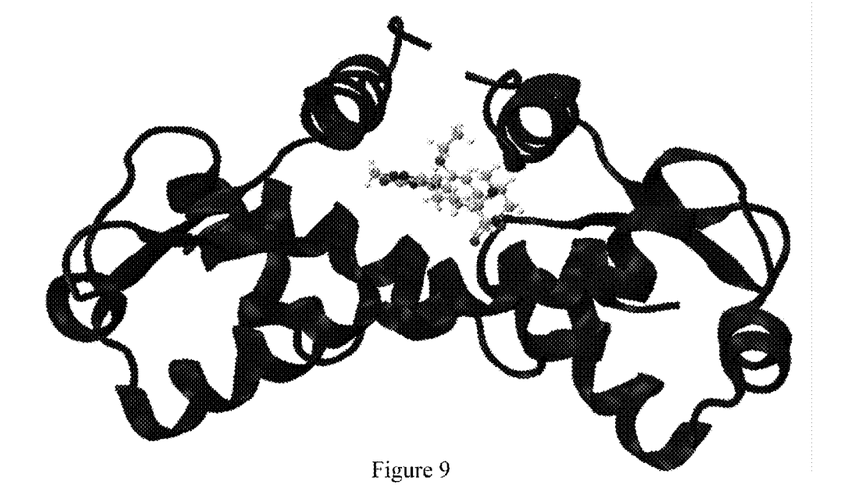
FIG. 9. The popular drug sildenafil docked into α5 binding pocket of CzrA.

The terms "binding pocket", "novel pocket", "candidate compound binding pocket" and "ligand binding pocket" may be used interchangeably and refer to the region described previously in the text. Examples of drug-like molecules bound to the drug pocket are shown in FIGS. 7, 8 and 9.

In an embodiment of the invention, Glide computer software by Schrodinger LLC is used to identify the compounds which would bind to and regulate metalloregulatory activity of the proteins of the ArsR/SmtB family by binding to the novel pocket. The Glide software program is described in U.S. Pat. No. 8,145,430, entitled "Predictive Scoring Function for Estimating Binding Affinity," which is hereby incorporated by reference in its entirety. The software programs which may be used in the current invention include but are not limited to:

MC SS, Ludi, QUANTA (macromolecular X-ray crystallography software); Insight II (biological compound modeling and simulation software); Cerius$^2$ (modeling and simulation software); CHARMm (software for simulation of biological macromolecules); Modeler from Accelrys, Inc. (San Diego, Calif.); AMBER and AmberTools suite of programs (Case et al., University of California, San Francisco); CHIMERA molecular modeling software (University of California, San Francisco), VIVID (visualization software); Gaussian 09 (electronic structure program); GAMESS (electronic structure program); SYBYL (molecular modeling software); Unity, FleXX, and LEAPFROG from TRIPOS, Inc. (St. Louis, Mo.); AUTODOCK (Scripps Research Institute, La Jolla, Calif.); GRID (Oxford University, Oxford, UK), DOCK (University of California, San Francisco, Calif.); Flo+ and Flo99 (Thistlesoft, Morris Township, N.J.); ROCS, ZAP, FRED, Vida, and Szybki from Openeye Scientific Software (Santa Fe, N. Mex.); Maestro and Macromodel from Schrodinger, LLC (Portland, Oreg.); MOE (Chemical Computing Group, Montreal, Quebec); Allegrow (Boston De Novo, Boston, Mass.); CNS (Brunger, et al., Acta Crystall. Sect. D 54:905-921, 1997); and GOLD (Jones et al., J. Mol. Biol. 245:43-53, 1995).

Structural information of a compound is provided as input to a docking program in order to screen the compound's ability to bind to a binding site (the binding pocket disclosed herein). Based on a pre-determined set of rules and instructions about binding interactions between a small molecule compound and the target binding site, the docking software program predicts the probability of the compound binding to the protein. This is followed by extensive molecular dynamics simulations using the AMBER program that investigate the ability of the drug molecule to regulate the activity and allosteric mechanism of the target protein. Commonly used binding interactions between a small molecule compound and a target binding site include, but are not limited to, hydrophilic interactions, hydrophobic interactions, van der Waals interactions, and hydrogen bonds.

In an aspect of this invention, protein structures obtained using restrained MD NMR refinement methods are used to supplement previously determined crystallographic and NMR structures of the protein in its various allosteric forms. In the restrained MD NMR refinement approach, the NMR-derived structure of the protein is refined using extensive MD simulations that are restrained used NMR-derived data. Such an approach utilizes a state-of-the-art electrostatics representation (particle mesh Ewald) to treat long-range electrostatics along with an explicit solvation model. To further refine specific parts of the protein structure, such as the metal ion binding site, a restrained QM/MM MD-based approach is utilized. Such an approach facilitates the calculation and provides an ensemble of structures that provide an accurate depiction of the protein structure in the solution phase.

In an aspect of the invention, the structural information about a binding pocket of a protein of the ArsR/SmtB family is provided as input to a docking program. In an embodiment of the invention, the structural information about the α5 metal ion binding site or the DNA binding site of a protein of the ArsR/SmtB family may also be provided to a docking program. A set of rules and instructions are also provided to the docking program about binding interactions between a small molecule compound and the binding pocket of a protein of the ArsR/SmtB family. Based on the structural information and the instructions, the docking program predicts the binding affinity of a particular small molecule compound for a binding pocket of a protein of the ArsR/SmtB family. A long molecular dynamics run on the docked drug structure predicts whether the propensity of the protein to remain in the metal ion bound open conformation, the DNA bound closed conformation, or the apo-form is higher when bound to the compound than the propensity of the protein to remain in the metal ion bound conformation, the DNA bound conformation, or the apo-conformation when not bound to the compound. A further aspect of the invention involves selecting the compound if the propensity of the protein of the ArsR/SmtB family to remain in the metal ion bound form, the DNA bound form, or the apo-form is higher when bound to the compound than the propensity of that protein to remain in the metal ion bound form, the DNA bound form, or the apo-form when not bound to the compound.

In another aspect of the invention, the docking program provides a "binding score" which indicates the strength of the binding between a compound and the binding pocket on a protein of the ArsR/SmtB family. Binding score can be calculated so that a higher binding score indicates stronger binding affinity. Binding score can also be calculated so that a higher binding score indicates weaker binding affinity. In an embodiment of the invention, only those compounds from the compound library are selected which have binding scores higher or lower than a pre-determined level.

Figure 10:
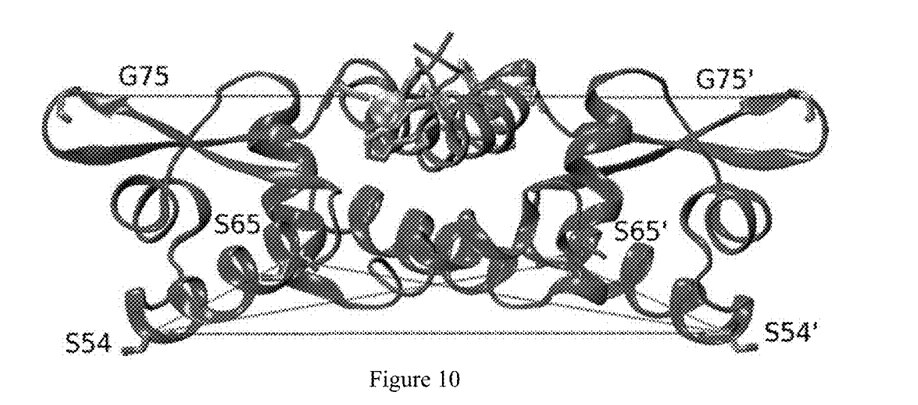
FIG. 10. Inter-protomer αR-αR' distances (S54-S54'), bend angle (S54-S65-S54' and S54'-S65'-S54) and β-wing to β-wing distance (G75-G75'). All distances and angles are measured based on the backbone alpha carbon distances.
Figure 11A:
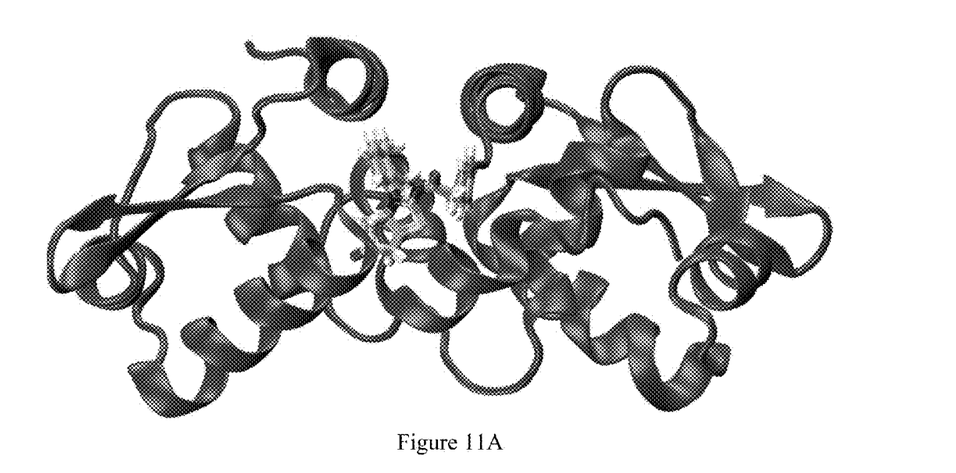
FIGS. 11A-11B. Impact of binding KMC drug-like molecule to CzrA. (a) The drug-like molecule docked into the binding pocket of CzrA in the "closed" conformation. (b)
Figure 11B:
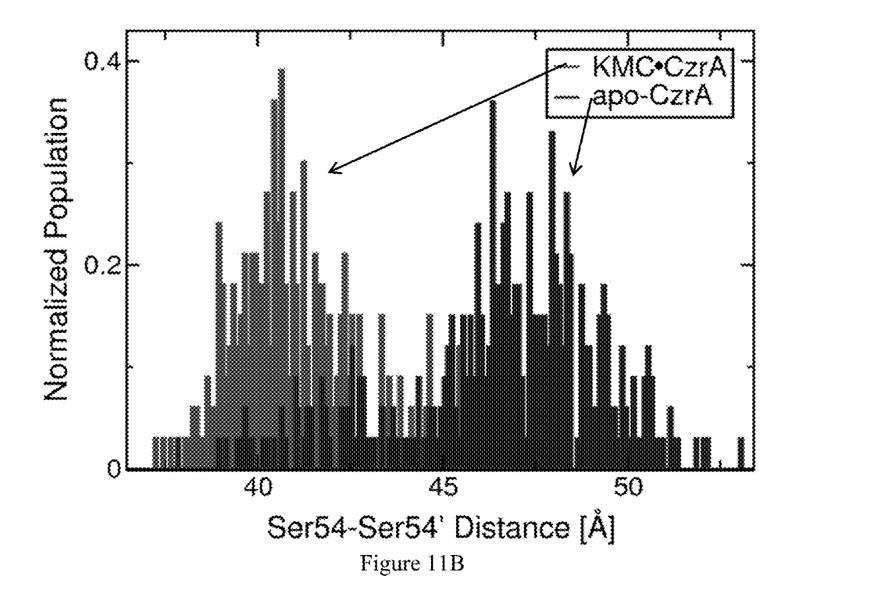

In another aspect of this invention, the complexed protein structure (protein and docked compound) is simulated using a classical MD approach. This approach may be utilized using any number of MD programs that are not limited to the AMBER suite of programs, CHARMM, GROMOS, GROMACS, TINKER, Desmond, DLPOLY, DLPROTEIN and LLAMPS. In the Amber suite of programs, the complexed protein structure was maintained in its biologically active dimer state and was immersed in a periodically replicated rectangular box of SPCE water molecules allowing for an 8 Å solvation shell around every protein atom (Jorgensen 2005). Force field parameters for the drug molecule were created using the GAFF approach. Charged amino acids were modeled in protonation states obtained from the H++ protonation state server (Gordon et al. 2005), while the metal-ligating residues were maintained in their metal-binding protonation states. Explicit Cl⁻ ions were added to neutralize the net charge on the solvated system (Joung and Cheatham 2008). Next, the solvated protein was energy minimized and equilibrated using a well-defined procedure (Chakravorty et al. 2009; Chakravorty et al. 2008; Chakravorty and Hammes-Schiffer 2010). In brief, a five-step energy minimization protocol was implemented to gradually minimize the protein in its solvation environment. At each step additional parts of the system were energy minimized. In the first stage of energy minimization, bad contacts involving water molecules and ions were removed, while the protein was kept restrained with a strong harmonic positional restraint. Subsequent steps involved energy minimizing the hydrogen atoms on the protein structure, followed by side-chain atoms, followed by the backbone amide groups. In the final step of energy minimization the entire solvated system was energy minimized simultaneously. A combination of conjugate-gradient and steepest-descent energy minimization algorithms was used at step in this scheme (Allen and Tildesley 1987). Next, a simulated annealing-like approach was implemented to equilibrate the energy minimized system. The solvated protein was gradually heated to 300K over 200 ns of MD for a canonical ensemble (NVT) (Allen and Tildesley 1987). The protein was further equilibrated for an isobaric and isothermal ensemble (NPT) for 1 ns at 1 atm pressure (Allen and Tildesley 1987). Following the equilibration phase, an MD simulation was propagated at 300K for hundreds of nanoseconds using a Langevin thermostat. A time step of 2 fs was employed during this simulation and frames were collected once for every 1000 steps of MD. Over the course of this simulation, long-range electrostatics were calculated using the particle mesh Ewald method (PME) and the system temperature was maintained using Langevin Dynamics (Allen and Tildesley 1987). The SHAKE algorithm was utilized to maintain heavy atom-hydrogen bond lengths and the translational center-of-mass motion was removed every 100 steps (Allen and Tildesley 1987). Such an approach can be modified based on the MD program and available options. The suitability of the compound is identified by measuring the inter-protomer $\alpha R$-$\alpha R'$ and $\beta$-wing to $\beta'$-wing distances. For CzrA, the $\alpha R$-$\alpha R'$ distances are measured between the two Ser54 protein backbone C$\alpha$ atoms and the $\beta$-wing to $\beta'$-wing distances are measured between the Gly 75 residues (FIG. 10). The protein's bend angle defined by the average of the angles described by the S54-S65-S54' and S54'-S65'-S54 backbone alpha carbon is used as another metric of the efficacy of the drug molecule in restricting the ability of the protein to sample multiple conformations. For example, 100 ns MD simulations show that the KMC drug-like molecule forces CzrA to sample the closed conformation of the protein, while the uncomplexed apo protein samples the open conformation. While this molecule does not achieve a high score by the docking program, the extended MD simulation clarifies its effect on the allosteric mechanism in CzrA.

A number of metal ions may bind to allosterically functional metal ion binding sites in ArsR/SmtB sensor proteins. In some embodiments, the metal ion may be a heavy metal. In various of these embodiments, the heavy metal ion can be one or more heavy metal ions selected from the group consisting of iron, cadmium, zinc, iron, copper, nickel, cobalt, mercury, arsenic, gold and silver.

In another embodiment of the invention a compound is designed based on the structure of a binding pocket of a protein of the ArsR/SmtB family. In a further aspect of the invention, the docking program or the investigator suggests modifications to a compound, wherein the modifications enhance the binding affinity between the compound and the corresponding binding pocket on a protein of the ArsR/SmtB family. Such modifications can be used to increase the binding affinity of a candidate compound which has been previously identified to bind to a binding pocket of a protein of the ArsR/SmtB family. For example, the modifications to the compound change the compound so that the propensity of the protein to remain in the metal ion bound form, the DNA bound form, or the apo-form is higher when bound to the modified compound than the propensity of the protein to remain in the metal ion bound form, the DNA bound form, or the apo-form when bound to the compound. These modifications include, but are not limited to, changing a side chain, a ring structure, a functional group, the stereoisomeric conformation, and/or the ionic charge of a compound.

In a further aspect of the invention, a compound library is screened in silico to identify candidate compounds that bind to a binding pocket on a protein of the ArsR/SmtB family. The activity of candidate compounds identified as binding to the binding pocket of a protein of the ArsR/SmtB family can then tested using a bioassay. A bioassay of the current invention may involve in vivo or in vitro testing of the ability of a compound to bind to and modulate the activity of the proteins of the ArsR/SmtB family. The bioassay of the current invention can be designed to check the effect of the binding of the compound on the metalloregulatory and allosteric properties of the proteins of the ArsR/SmtB family. The bioassay may also assess the ability of the candidate compound(s) to affect the viability of a microorganism containing proteins of the ArsR/SmtB family.

In an embodiment of the invention, the binding affinity of a compound to a binding pocket of a protein of the ArsR/SmtB family is estimated by co-crystallizing the compound with the protein, checking whether the compound binds to the binding site on the protein based on the crystal structure of the co-crystallized protein, and estimating whether the propensity of the protein to remain in the metal ion bound conformation, the DNA bound conformation, or the apo-conformation is higher when bound to the compound than the propensity of the protein to remain in the metal ion bound conformation, the DNA bound conformation, or the apo-conformation when not bound to the compound.

In another embodiment of the invention the binding affinity of a candidate compound to a binding pocket of the protein of the ArsR/SmtB family is estimated based on the inhibitory effect of the candidate compound on the metalloregulatory ability of bacteria that use a protein of the ArsR/SmtB family for metalloregulation. For example, the bioassay may be carried out by growing a bacterial culture in the presence or absence of a compound, comparing the growth rates of the bacterial culture in the presence or absence of the compound, and selecting the compound if the growth rate of the bacterial culture is substantially reduced in the presence of the compound. The growth rate of the bacterial culture is substantially reduced if the growth rate is reduced by at least about 10%. The slower growth of the bacterial culture in the presence of the compound compared to the growth of the bacterial culture in the absence of the compound indicates that the candidate compound may have therapeutic benefit for the treatment of diseases caused by the bacterial cell. Alternatively, the rate of influx or efflux of isotopic heavy metal ions can be compared between microorganisms treated with a candidate compound and untreated microorganisms.

In another embodiment of the invention, the bioassay of the invention is an in vitro binding assay where the binding affinity of a protein of the ArsR/SmtB family for a metal or a target DNA molecule is estimated in the presence and the absence of a candidate compound. For example, the bioassay may be carried out by mixing a metal ion binding protein of the ArsR/SmtB family with the metal or target DNA molecule in the presence or absence of the candidate compound and estimating the extent of binding of the metal ion binding protein with the metal or the target DNA molecule in the presence or absence of the compound. One can then select the candidate compound for further testing or for formulation into a composition for further testing if the binding of the metal ion binding protein with the metal ion or the target DNA is substantially reduced in the presence of the compound. The binding of the metal ion binding protein with the metal or the target DNA is substantially reduced if the binding is reduced by at least about 10%. For example, the lower extent of binding of the protein to the target DNA molecule in the presence of the compound compared to the binding of the protein to the target DNA molecule in the absence of the compound indicates that the propensity of the protein to remain in the metal ion bound form is higher when bound to the compound than the propensity of the protein to remain in the metal ion bound form when not bound to the compound. On the other hand, the lower extent of binding of the protein to the metal in the presence of the compound compared to the binding of the protein to the metal in the absence of the compound indicates that the propensity of the protein to remain in the DNA bound form is higher when bound to the compound than the propensity of the protein to remain in the DNA bound form when not bound to the compound.

Another aspect of the invention pertains to inhibiting bacterial growth by contacting the bacteria with a compound that binds to a metal ion binding protein of the ArsR/SmtB family and increases its propensity to remain in the metal ion bound form, the DNA bound form, or the apo-form. Various embodiments of the invention provide pharmaceutical compositions comprising the compounds that bind to a metal ion binding protein of the ArsR/SmtB family and increase its propensity to remain in the metal ion bound form, the DNA bound form, or the apo-form. An aspect of the invention also provides a method of treating a bacterial infection by administering to a subject suffering from the bacterial infection a pharmaceutically effective amount of the compound that binds to a metal ion binding protein of the ArsR/SmtB family and increase its propensity to remain in the metal ion bound form, the DNA bound form, or the apo-form.

Thus, the following non-limiting embodiments are provided:

1. A method of identifying a candidate compound that binds to a binding pocket of a protein of the ArsR/SmtB family of transcriptional factors, wherein the regulatory protein exists in a first allosteric form, a second allosteric form, and an apo-form, wherein the first allosteric form is a conformationally restricted form (metal ion bound form or di-sulfide bound form) and the second allosteric form is a DNA bound form, and the apo-form is devoid of either the metal or the DNA, the method comprising:

providing a computer program with information comprising:

a) structural information about a binding pocket of the metal ion binding protein of the ArsR/SmtB family of metal ion transcriptional factors having similar allosteric mechanisms, such as the MarR and NikR-like families of proteins, b) structural information of the compound, and c) a set of rules and instructions about binding interactions between the compound and the binding pocket of the transcriptional regulator protein, wherein, based on the information and the instructions provided to the computer program, the computer program predicts whether the binding of the compound to the transcriptional regulator protein increases its propensity to remain in the metal ion bound form, the DNA bound form, or the apo-form, and selecting the compound if the propensity of the protein to remain in the metal ion bound conformation, the DNA bound conformation, or the apo-conformation is higher when bound to the compound than the propensity of the protein to remain in the metal ion bound conformation, the DNA bound conformation, or the apo-conformation when not bound to the compound.

2. The method of embodiment 1, wherein the computer program predicts whether the binding of the compound to the metal ion binding protein increases the propensity of the protein to remain in the metal ion bound form.

3. The method of embodiment 1, wherein the computer program predicts whether the binding of the compound to the metal ion binding protein increases the propensity of the protein to remain in the DNA bound form.

4. The method of embodiment 1, wherein the computer program predicts whether the binding of the compound to the regulatory protein increases the propensity of the protein to remain in the apo-form.

5. The method of embodiment 1, wherein, the metal ion is a heavy metal ion.

6. The method of embodiment 5, wherein the metal ion is selected from the group consisting of Zn, Cu, Mn, Ru, Au, Hg, Au, Hg, Ag, Ni, Fe, Cd, As, and Co.

7. The method of embodiment 1, wherein the metal ion binding protein of the ArsR/SmtB family is selected from the group consisting of *Staphylococcus aureus* CzrA, *Staphylococcus aureus* p1258 CadC, *Mycobacterium tuberculosis* CsoR, *Mycobacterium tuberculosis* NmtR, and *Synechococcus* spp. SmtB. Additionally, the method of embodiment 1 includes metal ion transcriptional factors having similar allosteric mechanisms such as *Steptococcus pneumonia* AdcR of the MarR family of proteins, *Escherichia coli* CsoR and *Helicobacter pylori* NikR of the NikR-like family of proteins.

8. The method of embodiment 1, wherein the computer programs are Glide and AMBER.

9. The method of embodiment 1, the method further comprising modifying the selected compound wherein the propensity of the transcriptional regulator protein to remain in the metal ion bound conformation, the DNA bound conformation, or the apo-conformation is higher when bound to the modified compound than the propensity of the regulatory protein to remain in the metal ion bound conformation, the DNA bound conformation, or the apo-conformation when bound to the compound.

10. The method of embodiment 9, wherein the modifications comprise one or more of the following: changing a side chain, a ring structure, a functional group, the stereoisomeric conformation, and/or the ionic charge of a compound.

11. The method of embodiment 1, wherein said method further comprises contacting a bacterial cell with said selected compound and:
a) growing a bacterial culture in the presence or absence of said selected compound, comparing the growth rates of the bacterial culture in the presence or absence of said selected compound, and determining if the growth rate of the bacterial culture is substantially reduced in the presence of the compound; and/or
b) growing a bacterial culture in the presence or absence of said selected compound, and comparing the rate of influx or efflux of isotopic heavy metal ions between bacterial cells treated with a candidate compound and untreated microorganisms.

12. A compound identified to bind to the binding pocket of a transcriptional regulator protein by the method of embodiment 1.

13. A composition comprising the compound of embodiment 12 and pharmaceutically acceptable excipients.

14. A method of inhibiting bacterial growth by the contacting the bacteria with the compound of embodiment 12.

15. A method of treating a bacterial infection by administering a pharmaceutically effective amount of the compound of embodiment 12 to a subject suffering from the bacterial infection.

All patents, patent applications, provisional applications, and publications referred to or cited herein are incorporated by reference in their entirety, including all figures and tables, to the extent they are not inconsistent with the explicit teachings of this specification.

Following are examples, which illustrate procedures for practicing the invention. These examples should not be construed as limiting. All percentages are by weight and all solvent mixture proportions are by volume unless otherwise noted.

It should be understood that the examples and embodiments described herein are for illustrative purposes only and that various modifications or changes in light thereof will be suggested to persons skilled in the art and are to be included within the spirit and purview of this application. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

REFERENCES (1) Hood, M. I.; Skaar, E. P. *Nature Reviews Microbiology* 2012, 10, 525-37.
(2) Ma, Z.; Jacobsen, F. E.; Giedroc, D. P. *Chemical Reviews* 2009, 109, 4644-81.
(3) Guerra, A. J.; Giedroc, D. P. *Archives of biochemistry and biophysics* 2012, 519, 210-22.
(4) Lee, C. W.; Chakravorty, D. K.; Chang, F. M.; Reyes-Caballero, H.; Ye, Y.; Merz, K. M., Jr.; Giedroc, D. P. *Biochemistry* 2012, 51, 2619-29.
(5) Hood, M. I.; Mortensen, B. L.; Moore, J. L.; Zhang, Y. F.; Kehl-Fie, T. E.; Sugitani, N.; Chazin, W. J.; Caprioli, R. M.; Skaar, E. P. *Plos Pathogens* 2012, 8, e1003068, 1-17.
(6) Chakravorty, D. K.; Parker, T. M.; Guerra, A. J.; Sherrill, C. D.; Giedroc, D. P.; Merz, K. M., Jr. *Journal of the American Chemical Society* 2012, ASAP article.
(7) Chakravorty, D. K.; Wang, B.; Lee, C. W.; Giedroc, D. P.; Merz, K. M., Jr. *Journal of the American Chemical Society* 2012, 134, 3367-76.
(8) Giedroc, D. P.; Arunkumar, A. I. *Dalton Transactions* 2007, 3107-20.
(9) Arunkumar, A. I.; Campanello, G. C.; Giedroc, D. P. *Proceedings of the National Academy of Sciences of the U.S. Pat. No.* 2,009,106, 18177-82.
(10) Grossoehme, N. E.; Giedroc, D. P. *Journal of the American Chemical Society* 2009, 131, 17860-70.
(11) Ma, Z.; Cowart, D. M.; Ward, B. P.; Arnold, R. J.; DiMarchi, R. D.; Zhang, L. M.; George, G. N.; Scott, R. A.; Giedroc, D. P. *Journal of the American Chemical Society* 2009, 131, 18044-18045.
(12) Eicken, C.; Pennella, M. A.; Chen, X. H.; Koshlap, K. M.; VanZile, M. L.; Sacchettini, J. C.; Giedroc, D. P. *Journal of Molecular Biology* 2003, 333, 683-95.
(13) Pennella, M. A.; Shokes, J. E.; Cosper, N. J.; Scott, R. A.; Giedroc, D. P. *Proceedings of the National Academy of Sciences of the U.S. Pat. No.* 2,003,100, 3713-8.
(14) Guerra, A. J.; Dann, C. E.; Giedroc, D. P. *Journal of the American Chemical Society* 2011, 133, 19614-7.
(15) Reyes-Caballero, H.; Campanello, G. C.; Giedroc, D. P. *Biophysical chemistry* 2011, 156, 103-14.
(16) Scheuermann, T. H.; Li, Q.; Ma, H. W.; Key, J.; Zhang, L.; Chen, R.; Garcia, J. A.; Naidoo, J.; Longgood, J.; Frantz, D. E.; Tambar, U. K.; Gardner, K. H.; Bruick, R. K. *Nature chemical biology* 2013, 271-276.
(17) Rogers, J. L.; Bayeh, L.; Scheuermann, T. H.; Longgood, J.; Key, J.; Naidoo, J.; Melito, L.; Shokri, C.; Frantz, D. E.; Bruick, R. K.; Gardner, K. H.; Macmillan, J. B.; Tambar, U. K. *Journal of Medicinal Chemistry* 2013, 1739-1747.

We claim:
1. A method of identifying a candidate compound that binds to a binding pocket of a protein of the ArsR/SmtB family of transcriptional factors, wherein, the regulatory protein exists in a first allosteric form, a second allosteric form, and an apo-form, wherein the first allosteric form is a conformationally restricted form (metal ion bound form or di-sulfide bound form) and the second allosteric form is a DNA bound form, and the apo-form is devoid of either the metal or the DNA, the method comprising:

providing a computer program with information comprising:
a) structural information about a binding pocket of a protein of ArsR/SmtB family or metal ion transcriptional factors having similar allosteric mechanisms,
b) structural information of the compound, and
c) a set of rules and instructions about binding interactions between the compound and the binding pocket of the a protein belonging to the ArsR/SmtB family or metal ion transcriptional factors having similar allosteric mechanisms, wherein, based on the information and the instructions provided to the computer program, the computer program predicts whether the binding of the compound to the metal ion binding protein of ArsR/SmtB family or the metal ion transcriptional factor having similar allosteric mechanisms increases the propensity of the protein to remain in the metal ion bound form, the DNA bound form, or the apo-form, and selecting the compound if the propensity of the regulatory protein or the metal ion transcriptional factor to remain in the metal ion bound conformation, the DNA bound conformation, or the apo-conformation is higher when bound to the compound than the propensity of the protein or the metal ion transcriptional factor to remain in the metal ion bound conformation (or similar conformationally locked state), the DNA bound conformation, or the apo-conformation when not bound to the compound.

2. The method of claim 1, wherein the computer program predicts whether the binding of the compound to the metal ion binding protein of ArsR/SmtB family or the metal ion transcriptional factor having similar allosteric mechanisms increases the propensity of the protein to remain in the metal ion bound form.

3. The method of claim 1, wherein the computer program predicts whether the binding of the compound to the metal ion binding protein of ArsR/SmtB family or the metal ion transcriptional factor having similar allosteric mechanisms increases the propensity of the protein to remain in the DNA bound form.

4. The method of claim 1, wherein the computer program predicts whether the binding of the compound to the regulatory protein of ArsR/SmtB family or the metal ion transcriptional factor having similar allosteric mechanisms increases the propensity of the protein to remain in the apo-form.

5. The method of claim 1, wherein, the metal ion is a heavy metal ion.

6. The method of claim 1, wherein in the metal ion binding protein of ArsR/SmtB family is selected from the group consisting of *Staphylococcus aureus* CzrA, *Staphylococcus aureus* p1258 CadC, *Mycobacterium tuberculosis* CsoR, *Mycobacterium tuberculosis* NmtR, *Synechococcus* spp. SmtB or a metal ion transcriptional factor having similar allosteric mechanisms selected from *Steptococcus pneumonia* AdcR of the MarR family of proteins, *Escherichia coli* CsoR and *Helicobacter pylori* NikR.

7. The method of claim 1, wherein the computer programs are Glide and AMBER.

8. The method of claim 1, the method further comprising modifying the selected compound wherein the propensity of the protein to remain in the metal ion bound conformation, the DNA bound conformation, or the apo-conformation is higher when bound to the modified compound than the propensity of the protein to remain in the metal ion bound conformation, the DNA bound conformation, or the apo-conformation when bound to the compound.

9. The method of claim 8 wherein the modifications comprise one or more of the following: changing a side chain, a ring structure, a functional group, the stereoisomeric conformation, and/or the ionic charge of a compound.

10. The method of claim 1, wherein said method further comprises contacting a bacterial cell with said selected compound and:
a) growing a bacterial culture in the presence or absence of said selected compound, comparing the growth rates of the bacterial culture in the presence or absence of said selected compound, and determining if the growth rate of the bacterial culture is substantially reduced in the presence of the compound; and/or
b) growing a bacterial culture in the presence or absence of said selected compound, comparing the rate of influx or efflux of isotopic heavy metal ions between bacterial cells treated with a candidate compound and untreated microorganisms.

11. A compound identified to bind to the binding pocket of a protein of ArsR/SmtB family by the method of claim 1.

12. A composition comprising the compound of claim 11 and pharmaceutically acceptable excipients.

13. A method of inhibiting bacterial growth by the contacting the bacteria with the compound of claim 11.

14. A method of treating a bacterial infection by administering a pharmaceutically effective amount of the compound of claim 11 to a subject suffering from the bacterial infection.

* * * * *